(12) United States Patent
Nickel et al.

(10) Patent No.: US 7,517,872 B2
(45) Date of Patent: Apr. 14, 2009

(54) COMPOUNDS FOR THE TREATMENT OF HEPATITIS C

(75) Inventors: Andrew Nickel, New Haven, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/031,844

(22) Filed: Feb. 15, 2008

(65) Prior Publication Data

US 2008/0206191 A1 Aug. 28, 2008

Related U.S. Application Data

(60) Provisional application No. 60/891,049, filed on Feb. 22, 2007.

(51) Int. Cl.
*A61P 31/00* (2006.01)
*A61K 31/55* (2006.01)
*C07D 223/14* (2006.01)

(52) U.S. Cl. .................. 514/214.01; 540/576
(58) Field of Classification Search ............ 514/214.01; 540/576
See application file for complete search history.

(56) References Cited

U.S. PATENT DOCUMENTS

| 7,153,848 B2 | 12/2006 | Hudyma et al. | 514/214.01 |
| 7,348,425 B2 | 3/2008 | Hudyma et al. | 540/576 |
| 2007/0060565 A1 | 3/2007 | Meanwell et al. | 514/214.01 |
| 2007/0078122 A1 | 4/2007 | Bergstrom et al. | 514/214.01 |
| 2007/0184024 A1 | 8/2007 | Meanwell et al. | 424/85.2 |
| 2007/0185083 A1 | 8/2007 | Bergstrom et al. | 514/214.01 |
| 2007/0270405 A1 | 11/2007 | Bender et al. | 514/214.01 |
| 2007/0270406 A1 | 11/2007 | Gentles et al. | 514/214.01 |
| 2007/0275930 A1 | 11/2007 | Gentles et al. | 514/79 |
| 2007/0275947 A1 | 11/2007 | Bergstrom | 514/211.15 |
| 2007/0287694 A1 | 12/2007 | Yeung et al. | 514/210.21 |

FOREIGN PATENT DOCUMENTS

| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 12/022,541, filed Jan. 30, 2008, Kap-Sun Yeung et al.
U.S. Appl. No. 12/046,030, filed Mar. 11, 2008, Kap-Sun Yeung et al.
U.S. Appl. No. 12/039,239, filed Feb. 28, 2008, Robert G. Gentles et al.
U.S. Appl. No. 12/045,874, filed Mar. 11, 2008, Robert G. Gentles et al.
U.S. Appl. No. 12/045,766, filed Mar. 11, 2008, John A. Bender et al.
U.S. Appl. No. 12/041,072, filed Mar. 3, 2008, Kap-Sun Yeung et al.
U.S. Appl. No. 12/046,286, filed Mar. 11, 2008, Piyasena Hewawasam et al.
U.S. Appl. No. 11/942,285, filed Nov. 19, 2007, John A. Bender et al.
U.S. Appl. No. 11/971,362, filed Jan. 9, 2008, John A. Bender et al.

*Primary Examiner*—Brenda L Coleman
(74) *Attorney, Agent, or Firm*—James Epperson

(57) ABSTRACT

The invention encompasses compounds of formula I as well as compositions and methods of using the compounds. The compounds have activity against hepatitis C virus (HCV) and are useful in treating those infected with HCV.

13 Claims, No Drawings

COMPOUNDS FOR THE TREATMENT OF HEPATITIS C

CROSS REFERENCE TO RELATED APPLICATIONS

This application claims the benefit of U.S. provisional application Ser. No. 60/891,049, filed Feb. 22, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

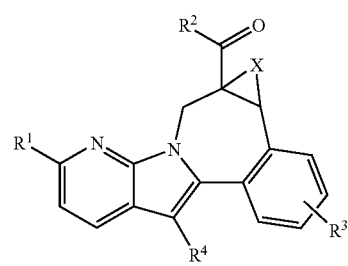

where:

$R^1$ is H, $CO_2R^5$ or $CONR^6R^7$;

$R^2$ is hydroxy, alkoxy, amino, alkylamino, dialkylamino;

or $R^2$ is azetidinyl, pyrrolidinyl, piperidinyl, piperazinyl, morpholinyl, homopiperidinyl, or homomorpholinyl, and is substituted with 0-3 substituents selected from alkyl and alkoxy;

or $R^2$ is

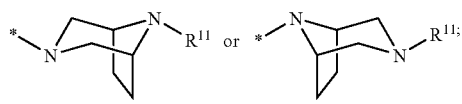

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, $alkylSO_2$, $cycloalkylSO_2$, $haloalkylSO_2$, $(R^8)_2NSO_2$, or $(R^9)SO_2$;

$R^7$ is hydrogen or alkyl;

$R^8$ is hydrogen or alkyl;

$R^9$ is azetidinyl, pyrrolidinyl, piperidinyl, N-($R^{10}$)piperazinyl, morpholinyl, thiomorpholinyl, homopiperidinyl, or homomorpholinyl;

$R^{10}$ is hydrogen or alkyl;

$R^{11}$ is hydrogen, alkyl, cycloalkyl, (cycloalkyl)alkyl, benzyl, alkylcarbonyl, alkoxycarbonyl, benzyloxycarbonyl, $(R^7)_2$NCO, $alkylSO_2$, or pyridinyl; and X is absent (forming a compound of formula Ia), a bond (forming a compound of formula Ib), or methylene (forming a compound of formula Ic);

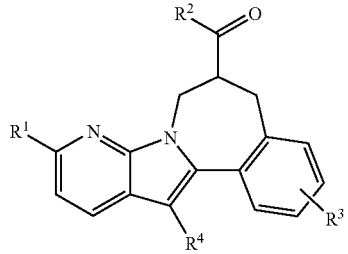
(Ia)

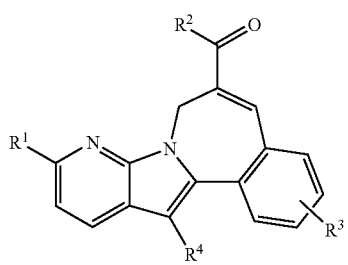
(Ib)

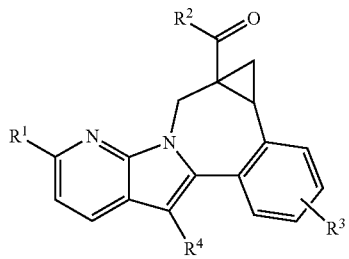
(Ic)

or a pharmaceutically acceptable salt thereof.

Another aspect of the invention is a compound of formula I where $R^1$ is $CONR^6R^7$; $R^6$ is alkyl$SO_2$, cycloalkyl$SO_2$, haloalkyl$SO_2$, $(R^8)_2NSO_2$, or $(R^9)SO_2$; and $R^7$ is hydrogen.

Another aspect of the invention is a compound of formula I where $R^2$ is dimethylamino, pyrrolidinyl, morpholinyl, dimethylmorpholinyl, piperazinyl, trimethylpiperazinyl, or

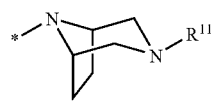

where $R^{11}$ is methyl.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^8)_2NSO_2$ or $(R^9)SO_2$.

Another aspect of the invention is a compound of formula I where X is absent (formula Ia).

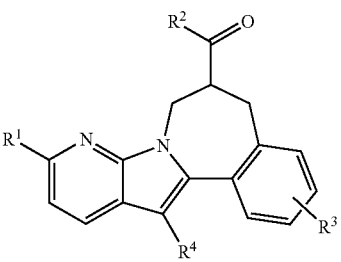
(Ia)

Another aspect of the invention is a compound of formula I where X is a bond (formula Ib).

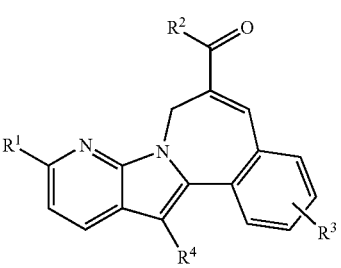
(Ib)

Another aspect of the invention is a compound of formula I where X is methylene (formula Ic).

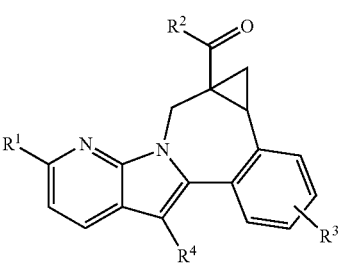
(Ic)

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents.

These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

Synthetic Method

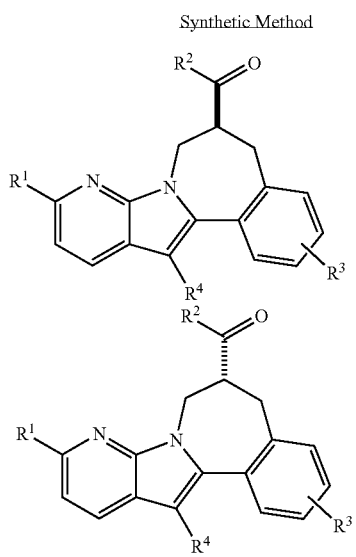

The compounds may be made by methods known in the art including those described below. Some reagents and intermediates are known in the art. Other reagents and intermediates can be made by methods known in the art using readily available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art. Scheme 1 describes some methods to prepare the compounds of Scheme 1. Schemes 2, 3, and 4 and the experimental section provides alternative methods for preparing some of the compounds.

As shown in Scheme 1, the conversion of the N-oxide to the C(O)NR$^6$R$^7$ amide, the carboxylic acid product obtained from the lithiation/trapping of CO$_2$ reaction can be condensed with a variety of sulfonyl ureas, (or as shown in Scheme 1 primary or secondary sulfonamides) using for example, 1,1'-carbonyldiimidazole in combination with 1,8-diazabicyclo[5.4.0]undec-7-ene in anhydrous THF. Typically, the diimidazole is added to a solution of the acid in THF and then the solution is heated. The sulfamide or sulfonamide is added followed by base addition (for example, DBU) and then heating is continued until the coupling reaction is judged to be complete. Alternatively, 2-bromo-3-cyclohexyl-1H-pyrrolo[2,3-b]pyridine may be reacted directly with the 2-boronic acid benzaldehyde.

Scheme 1.

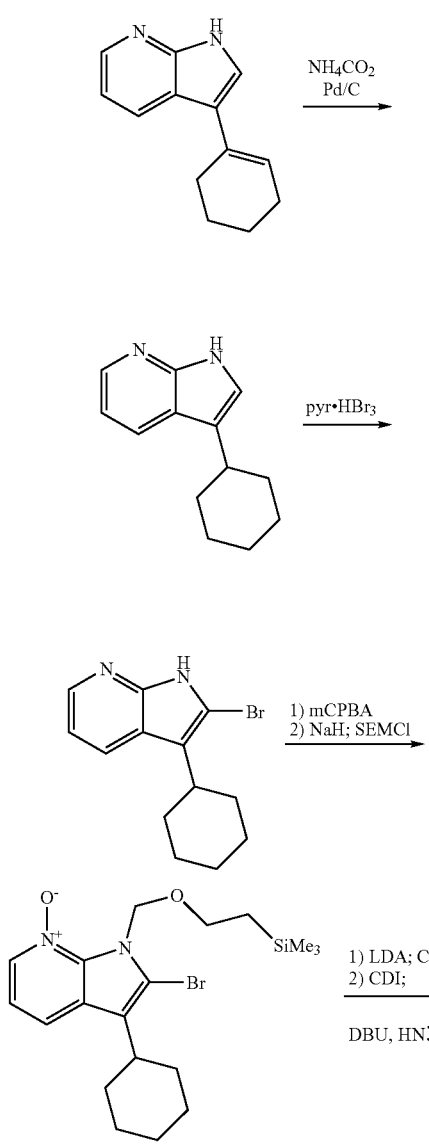

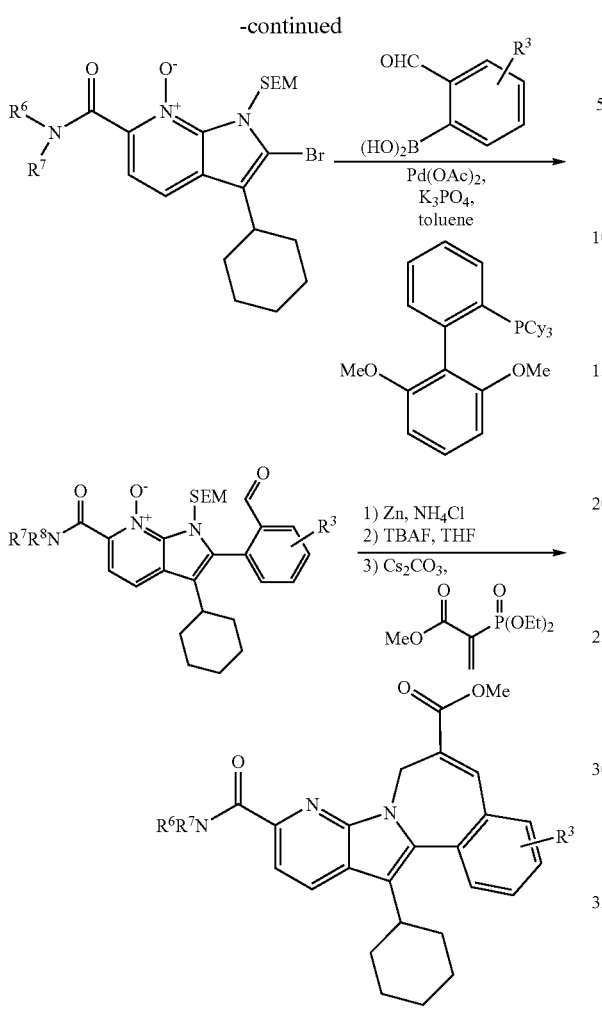

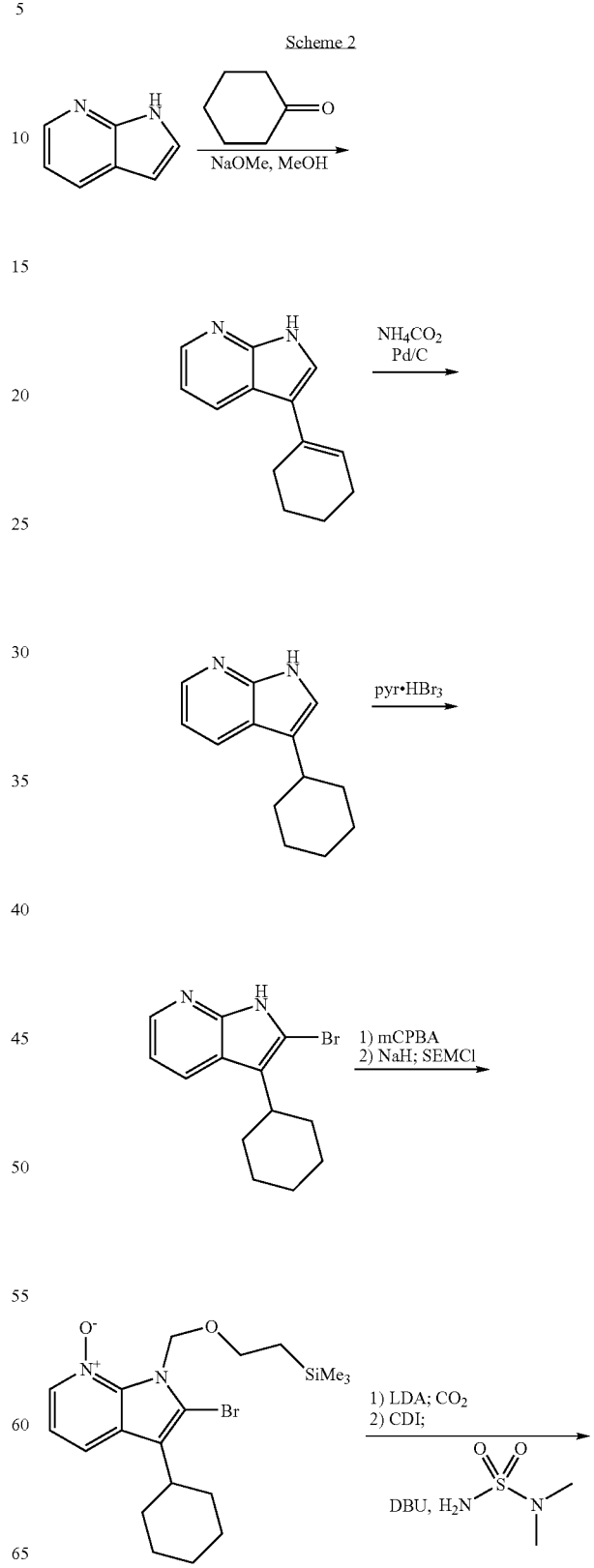

3-Cyclohexyl-1H-pyrrolo[2,3-b]pyridine can be brominated to 2-bromo-3-cyclohexyl-1H-pyrrolo[2,3-b]pyridine (see Scheme 2). Oxidation at N-7 can be effected using, for example, mCPBA, and N-1 can then be protected as its (2-(trimethylsilyl)ethoxy)methyl aminal by treatment with sodium hydride and (2-(chloromethoxy)ethyl)trimethylsilane. The resultant N-oxide can then be deprotonated at C-6 by a strong base such as lithium diisopropyl amide and the resulting anion quenched by electrophiles such as carbon dioxide. This carboxylic acid can be condensed with a variety of sulfonyl ureas, (or as shown in Scheme 1 primary or secondary sulfonamides) using for example, 1,1'-carbonyldiimidazole in combination with 1,8-diazabicyclo[5.4.0]undec-7-ene in anhydrous THF. Typically the diimidazole is added to a solution of the acid in THF and then the solution is heated. The sulfamide or sulfonamide is added followed by base (for example, DBU) and then heating is continued until the coupling reaction is judged to be complete. These compounds can be subjected to known coupling reactions with a diversity of 2-formyl boronic acids or esters, using for example, Suzuki coupling conditions, to provide aryl aldehydes of the type depicted. Reduction of the N-oxide can then be accomplished using standard conditions, for example, zinc dust and ammonium chloride in aqueous THF. Removal of the (2-(trimethylsilyl)ethoxy)methyl group can be accomplished under the action of tetrabutylammonium fluoride and the resulting hemiaminals can be converted to benzazepine derivatives by treatment with methyl 2-(diethoxyphosphoryl)acrylate under the influence of cesium carbonate in DMF via consecutive conjugate addition and Horner Emmons reactions.

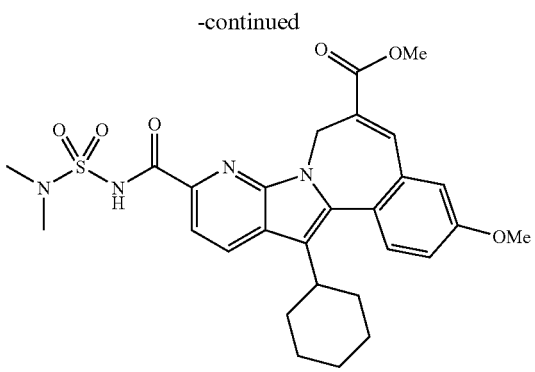
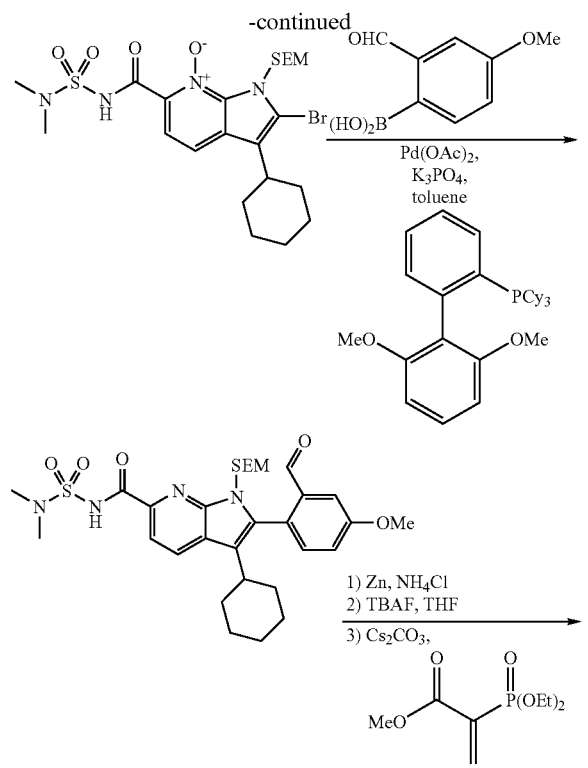

The benzazepine-derived esters described above can be hydrolyzed and the product acids can be condensed with a variety of secondary amines (see Scheme 3). Alternatively, the benzazepine-derived esters can also be converted to fused cyclopropyl derivatives by methods known in the art, including treatment of the unsaturated esters with trimethyl sulfoxonium iodide under strongly basic conditions in DMSO. The residual aliphatic ester moiety in the resultant fused cyclopropanes can be hydrolyzed and the product acids can be condensed with a variety of amines. The acyl sulfamide moiety in these amides can be alkylated, for example under Mitsunobu reaction conditions with triphenylphosphine, diethyl azodicarboxylate, and methanol in tetrahydrofuran solvent.

Scheme 3.

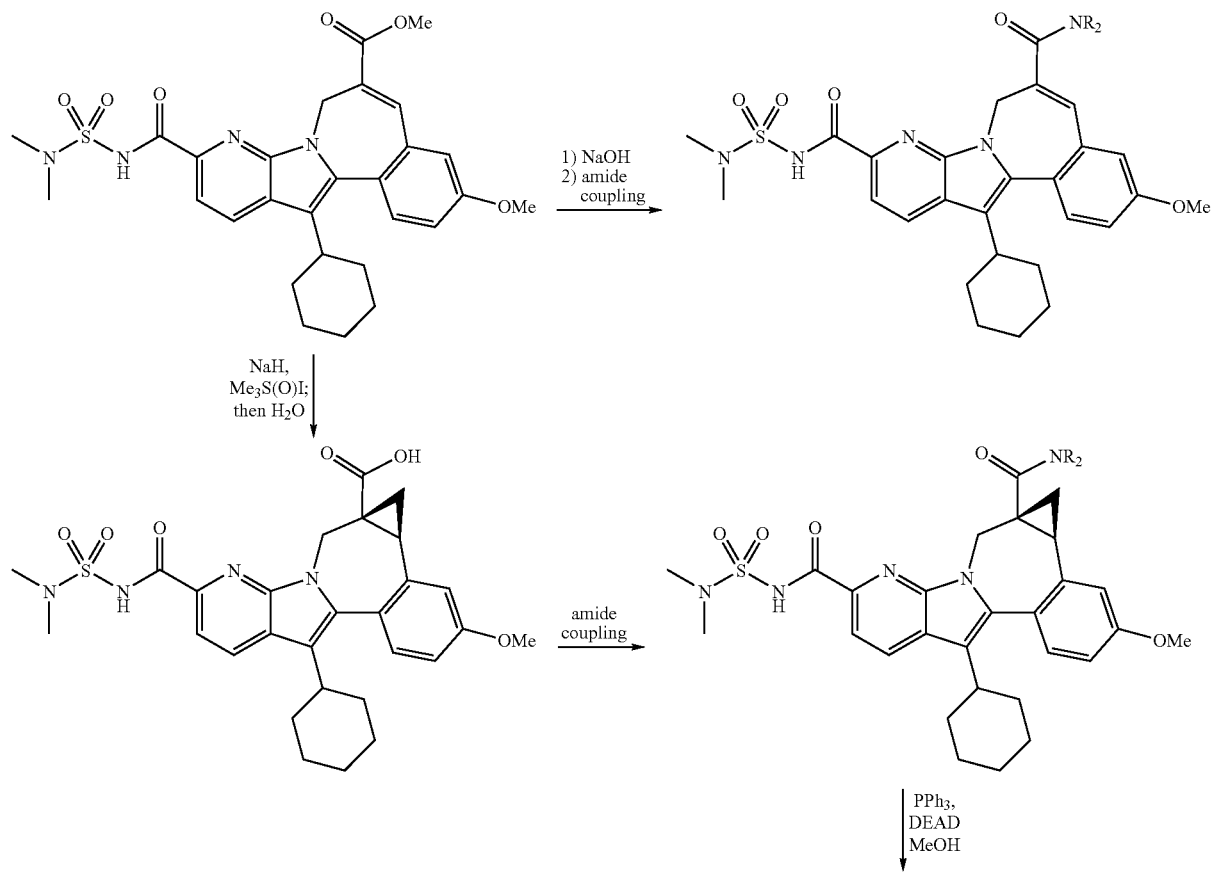

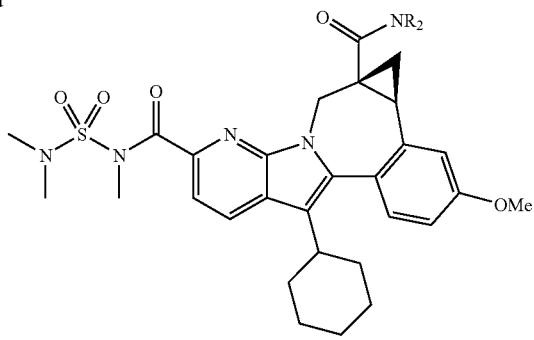

An alternative preparation for some formula I compounds is described in Scheme 4. Alkylation of 3-cyclohexyl-1H-pyrrolo[2,3-b]pyridine at N-7 can be effected under the action of sodium hydride and benzyl bromide. The resulting protected pyrrolopyridyl bromide is reactive toward known coupling reactions with a diversity of 2-formyl boronic acids or esters, for example, a Suzuki reaction to provide aryl aldehydes of the type depicted. Debenzylation can be effected under known conditions, such as heterogenous hydrogenation conditions with palladium hydroxide under an atmosphere of hydrogen gas. The resulting deprotected product can be converted to the corresponding benzazepine derivative by a cyclization protocol such as treatment with methyl 2-(diethoxyphosphoryl)acrylate in the presence of cesium carbonate in DMF. The ester product of this cyclization can be saponified and the resultant acid can be condensed with a variety of secondary amines.

Scheme 4.

Biological Methods

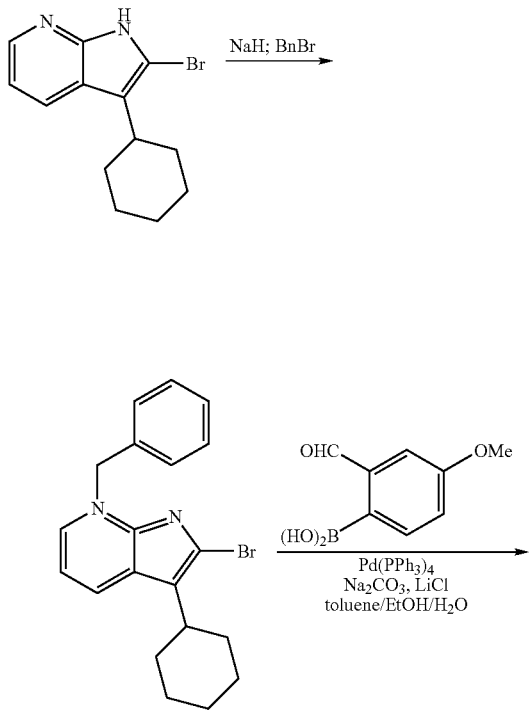

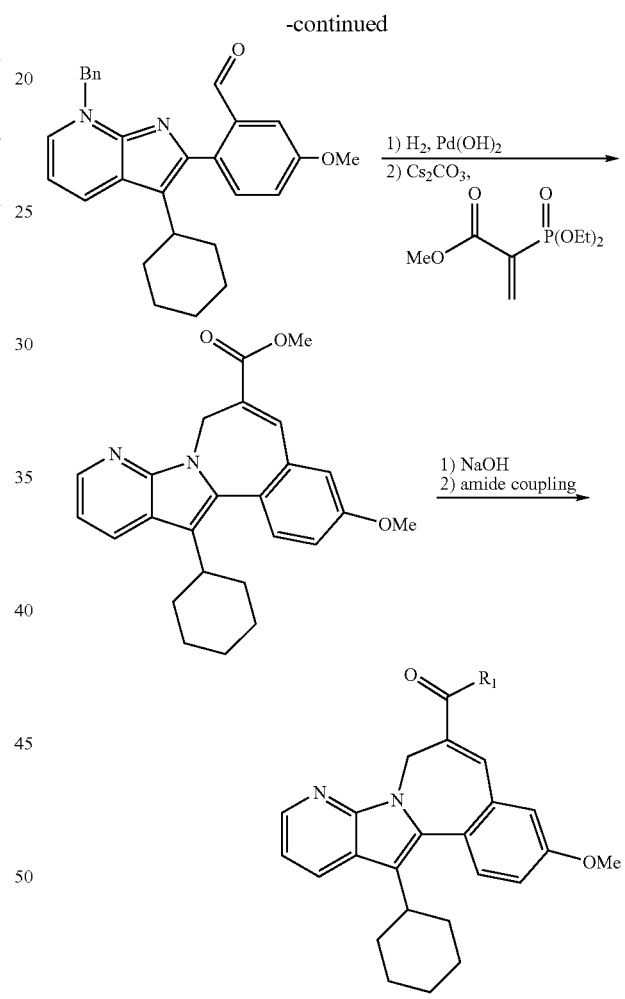

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., Anal. Biochem. 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 µM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naive Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.
TABLE 1
| Structure | IC$_{50}$ | EC$_{50}$ |
|---|---|---|
| 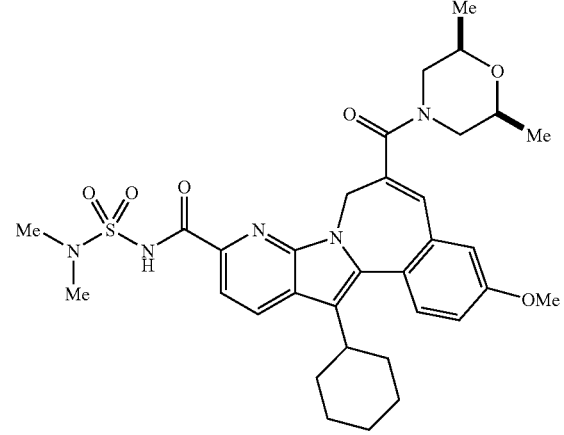 | B | A |
| 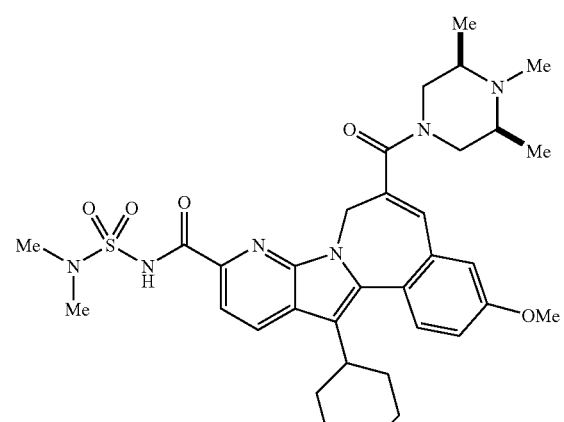 | B | B |
| 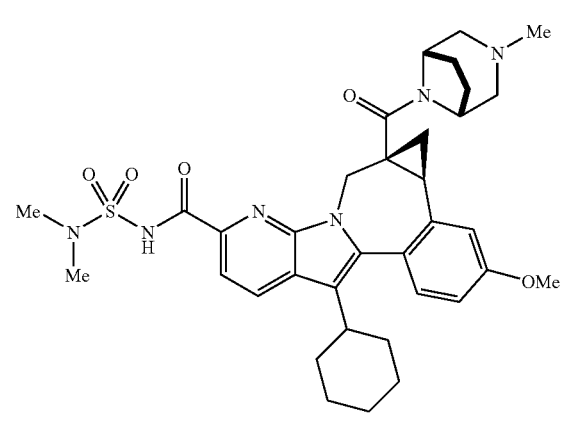 | B | F |

TABLE 1-continued
| Structure | IC$_{50}$ | EC$_{50}$ |
|---|---|---|
| 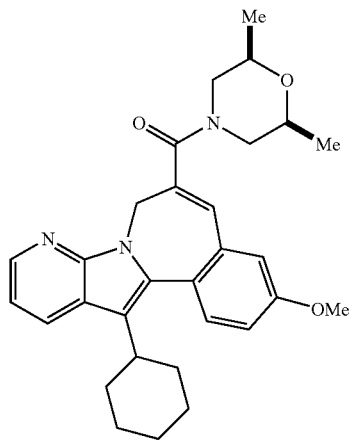 | E | D |
| 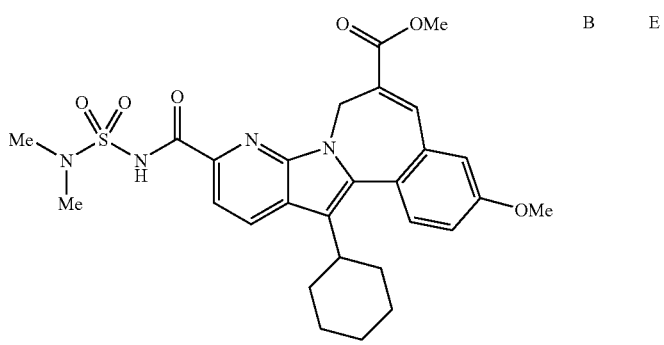 | B | E |
| 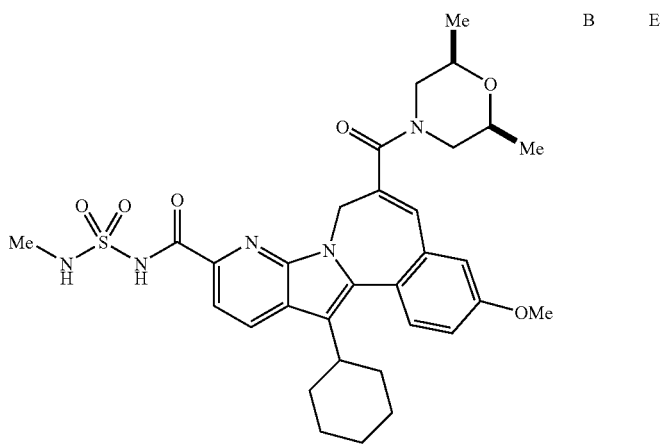 | B | E |

TABLE 1-continued

| Structure | IC$_{50}$ | EC$_{50}$ |
|---|---|---|
| [chemical structure] | E | F |

A >0.5 μM;
B 0.001 μM-0.5 μM;
C <0.02 μM but an exact value was not determined;
D >0.37 μM E 0.5 μM-10 μM but an exact value was not determined.
F >0.1 μM but an exact value was not determined
IC$_{50}$ values were determined using the preincubation protocol.
EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgment.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |

TABLE 2-continued

| Brand Name | Type of Inhibitor or Target | Source Company |
|---|---|---|
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Unless otherwise specified, analytical LC/MS data on the following intermediates and examples were acquired using the following columns and conditions. Stop time: Gradient+1 minute; Starting con: 0% B unless otherwise noted; Final conc: 100% B unless otherwise noted; Eluent A: 10% MeOH/ 90% H₂O with 0.1% TFA; Eluent B: 90% MeOH/10% H₂O with 0.1% TFA; Column: Phenomenex-Luna 10 μm C18, 50 mm×3.0 mm; Flow Rate: 4 ml/min; Gradient time: 2 min.

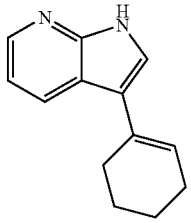

Intermediate 1

3-cyclohexenyl-1H-pyrrolo[2,3-b]pyridine. Methanol (150 mL) was added dropwise to a chilled (0° C.) 1 L flask containing sodium hydride (60% dispersion in mineral oil, 19.3 g, 480 mmol). To the stirred suspension was added 7-azaindole (10.2 g, 86 mmol) in MeOH (100 mL) and cyclohexanone (35 mL, 340 mmol) in MeOH (65 mL). The cloudy solution was refluxed for 24 h, then the solvent was removed under reduced pressure. The oily residue was cooled in an ice bath and 3 N HCl was added with vigorous stirring until the pH=8 (pH paper). The resulting yellow ppt. was collected by filtration, washed with H₂O, triturated with tBME/C₆H₁₄ (1:1, 50 mL), and dried by toluene azeotrope to give the title compound as a white solid (13.0 g, 76% yield). $^1$H NMR (400 MHz, CDCl$_3$) δ ppm 1.66-1.78 (m, 2H) 1.78-1.91 (m, 2H) 2.20-2.35 (m, 2H) 2.47 (d, J=1.76 Hz, 2H) 6.28 (d, J=3.78 Hz, 1H) 7.10 (dd, J=8.06, 4.78 Hz, 1H) 7.34 (s, 1H) 8.25 (dd, J=8.06, 1.26 Hz, 1H) 8.33 (dd, J=4.66, 1.39 Hz, 1H) 11.8 (br s, 1H); $^{13}$C NMR (100 MHz, CDCl$_3$) δ ppm 22.43, 22.98, 25.65, 27.88, 115.52, 117.31, 118.32, 121.57, 122.16, 129.39, 131.07, 141.99, 149.53.

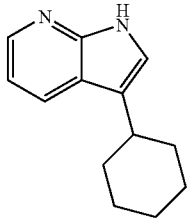

Intermediate 2

3-cyclohexyl-1H-pyrrolo[2,3-b]pyridine. To a suspension of Intermediate 1 (12.7 g, 64 mmol) in EtOH/THF (2:1, 200 mL) under a N₂ atmosphere was added Pd(OH)₂/C (20% w/w Pd, 900 mg). The flask was purged with H₂ and the reaction was stirred vigorously under a balloon of H₂ for 24 h, at which point an additional 1.5 g of catalyst was added. The slurry was stirred for 3 days, 700 mg additional catalyst was added, and the reaction was allowed to stir for 2 additional days, then filtered through Celite (THF rinse) and the filtrate concentrated to give the product as an off-white solid (6.6 g, 52% yield). LC/MS (ESI) retention time: 2.14 min, m/z 201 (MH⁺); $^1$H NMR (400 MHz, CDCl$_3$) δ ppm 1.21-1.36 (m, 1H) 1.38-1.54 (m, 4H) 1.73-1.81 (m, 1H) 1.85 (m, 2H) 2.01-2.12 (m, 2H) 2.69-2.88 (m, 1H) 6.99-7.09 (m, 2H) 7.96 (dd, J=8.06, 1.26 Hz, 1H) 8.19-8.32 (m, 1H) 9.29 (s, 1H).

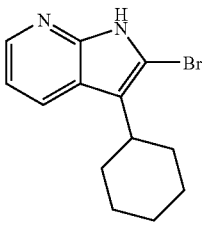

Intermediate 3

2-Bromo-3-cyclohexyl-1H-pyrrolo[2,3-b]pyridine. To a stirred suspension of Intermediate 2 (3.33 g, 16.5 mmol) in THF (9 mL) was added pyridinium hydrobromide perbromide (9 g, 28 mmol) and the resulting suspension was brought to reflux. After 4 h, the reaction was cooled to r.t. and quenched by the addition of sat'd $Na_2S_2O_3$ (30 mL), diluted with $H_2O$ (50 mL) and poured into $CH_2Cl_2$ (50 mL). The pH of the aqueous phase was brought to 10 (pH paper) by the addition of 1 N NaOH, and the aqueous phase was extracted with $CH_2Cl_2$ (4×50 mL). The combined organic phases were washed with $H_2O$ and brine, dried over $Na_2SO_4$, and concentrated to give a brown oil. MeOH (20 mL) was added, the flask was cooled in an ice bath, and the resulting precipitate was collected by filtration. Trituration with cold MeOH afforded 1.3 g (28% yield) of the title compound as a brown powder. LC/MS (ESI) retention time: 1.66 min, m/z 279, 281 (MH$^+$); $^1$H NMR (400 MHz, CDCl$_3$) δ ppm 1.26-1.52 (m, 3H) 1.75-1.94 (m, 7H) 2.72-2.93 (m, 1H) 7.04 (dd, J=8.06, 4.78 Hz, 1H) 8.02 (dd, J=8.06, 1.51 Hz, 1H) 8.26 (dd, J=4.78, 1.51 Hz, 1 H).

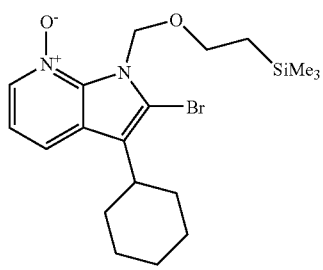

Intermediate 4

2-Bromo-3-cyclohexyl-1-((2-(trimethylsilyl)ethoxy)methyl)-1H-pyrrolo[2,3-b]pyridine 7-oxide. To a solution of Intermediate 3 (330 mg, 1.2 mmol) in 1,2-dimethoxyethane (11 mL) was added mCPBA (225 mg, 1.3 mmol) and the reaction was allowed to stir at r.t. for 1 h before the volume was reduced to ~4 mL. $H_2O$ was added and the suspension basified to pH=9 (pH paper) with 1 N NaOH and sat'd $NaHCO_3$. The reaction was extracted with EtOAc (2×, 225 mL total), and the combined organic phases were washed with brine and dried over $Na_2SO_4$. Concentration yielded 450 mg of a crude yellow foam, which was suspended in DMF (2 mL). NaH (60% dispersion in mineral oil, 100 mg, 2.5 mmol) was added which caused the immediate evolution of gas. After stirring for 10 min at r.t., SEMCl (250 μL, 1.4 mmol) was added dropwise via syringe. The resulting solution was stirred at r.t. for 2 h, then poured into EtOAc/$H_2O$ (100 mL/50 mL). The organic phase was washed with $H_2O$ (3×15 mL) and brine, dried over $Na_2SO_4$, filtered, and concentrated. Chromatography on silica gel (gradient elution: 5%→100% EtOAc in $C_6H_{14}$ over 1 L) afforded the product as an oil (213 mg, 42% yield from 2). LC/MS (ESI) retention time: 2.19 min, m/z 425, 427 (MH$^+$); $^1$H NMR (400 MHz, CDCl$_3$) δ ppm −0.18 (s, 9H) 0.71-0.80 (m, 2H) 1.20-1.27 (m, 1H) 1.28-1.43 (m, 2H) 1.64-1.84 (m, 7H) 2.71-2.88 (m, 1H) 3.50-3.69 (m, 2H) 6.34 (s, 2H) 6.89 (dd, J=8.24, 6.41 Hz, 1H) 7.55 (d, J=8.24 Hz, 1H) 7.96 (d, J=6.41 Hz, 1H).

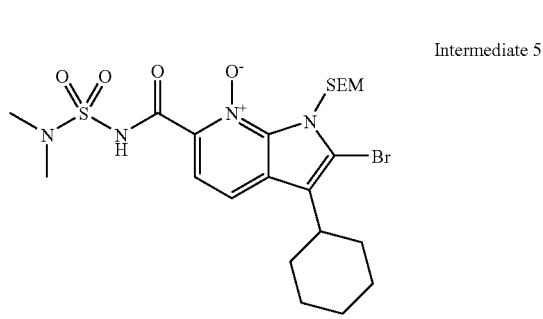

Intermediate 5

2-Bromo-3-cyclohexyl-6-(N,N-dimethylsulfamoylcarbamoyl)-1-((2-(trimethylsilyl)ethoxy)methyl)-1H-pyrrolo[2,3-b]pyridine 7-oxide. A solution of Intermediate 4 (1.66 g, 3.9 mmol) in anhydrous THF (30 mL) was cooled to −78° C. and LDA (1.8 M in THF/PhEt/$C_7H_{16}$, 8.6 mL, 15.5 mmol) was added dropwise via syringe. After stirring at −78° C. for 30 min, the reaction was poured directly onto freshly crushed dry ice. A vigorous foaming ensued, and the solution was allowed to stir until gas evolution ceased. The reaction was then partitioned between $CH_2Cl_2$ (300 mL) and 1 N HCl (25 mL). The resulting emulsion was washed with $H_2O$ and brine, filtered, and washed with brine again. The organic solution was dried by EtOH azeotrope to afford a brown gum, which dissolved in THF (10 mL). Carbonyl diimidazole (1.5 g, 9.3 mmol) was added and the solution warmed to 50° C. under a $N_2$ atmosphere for 2 h. After cooling to r.t., N,N-dimethyl sulfamide (1.2 g, 9.7 mmol) and 1,8-diazabicyclo[5.4.0]undec-7-ene (1.6 mL, 10.5 mmol) were added and the reaction allowed to stir at r.t. for 2.5 h before being diluted with EtOAc (300 mL). The organic solution was washed with 1 N HCl (2×10 mL), $H_2O$ (10 mL), and brine, dried ($Na_2SO_4$), filtered, and concentrated to give a brown oil, which was dissolved in $CH_2Cl_2$ (3 mL). Hexanes (10 mL) was added, and the resulting yellow ppt. was removed by filtration (1:1 $CH_2Cl_2/C_6H_{14}$ rinse). The filtrate was concentrated to give a brown foam. Chromatography on silica gel (gradient elution, 10%→100% EtOAc in $C_6H_{14}$ over 550 mL, then 100% for 200 mL) afforded the title compound (745 mg, 33% yield from Intermediate 4) as a brown foam. LC/MS (ESI) retention time: 2.26 min, m/z 575, 577 (MH$^+$); $^1$H NMR (400 MHz, CDCl$_3$) δ ppm −0.08 (s, 9H) 0.85-0.92 (t, J=8.2 Hz, 2H) 1.28-1.49 (m, 3H) 1.75-1.95 (m, 7H) 2.83-2.95 (m, 1H) 3.03 (s, 6H) 3.62-3.72 (m, 2H) 6.32 (s, 2H) 7.81 (d, J=8.56 Hz, 1H) 8.10 (d, J=8.56 Hz, 1H) 14.49 (s, 1H).

Intermediate 6

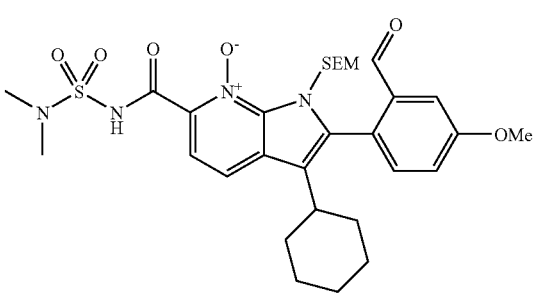

3-Cyclohexyl-6-(N,N-dimethylsulfamoylcarbamoyl)-2-(2-formyl-4-methoxyphenyl)-1-((2-(trimethylsilyl)ethoxy)methyl)-1H-pyrrolo[2,3-b]pyridine 7-oxide. Potassium phosphate (830 mg, 3.9 mmol), 2-formyl-4-methoxyphenylboronic acid (470 mg, 2.6 mmol), palladium (II) acetate (44 mg, 65 μmol), and 2-dicyclohexylphosphino-2',6'-dimethoxybiphenyl (70 mg, 170 μmol) were added to a solution of Intermediate 5 in toluene (13 mL). The heterogeneous mixture was brought to reflux under $N_2$ for 2 h, then allowed to cool to r.t. and $H_2O$ (25 mL) was added. The biphasic mixture was poured into EtOAc (200 mL), and a black emulsion formed. The mixture was filtered through filter paper (EtOAc rinse), the organic phase was collected, and the aqueous phase re-extracted with EtOAc. The combined organic phases were washed with $H_2O$ (20 mL) and brine, dried over $Na_2SO_4$, filtered, and concentrated. Chromatography on silica gel (gradient elution: 10%→20% EtOAc in $C_6H_{14}$ over 800 mL, then→100% EtOAc over 200 mL) afforded 475 mg of the title compound (58% yield). LC/MS (ESI) retention time: 2.20 min, m/z 631 (MH+); $^1$H NMR (400 MHz, CDCl$_3$) δ ppm −0.09 (s, 9H) 0.68-0.84 (m, 2H) 1.16 (s, 3H) 1.50-1.64 (m, 2H) 1.64-1.80 (m, 5H) 2.40-2.50 (m, 1H) 3.04 (s, 6 H) 3.41-3.49 (m, 2H) 3.96 (s, 3H) 5.37 (d, J=9.82 Hz, 1H) 6.27 (d, J=9.82 Hz, 1 H) 7.27 (d, J=2.52 Hz, 1H) 7.30-7.35 (m, 1H) 7.59 (d, J=2.77 Hz, 1H) 7.87 (d, J=8.56 Hz, 1H) 8.15 (d, J=8.56 Hz, 1H) 9.66 (s, 1H) 14.69 (s, 1H).

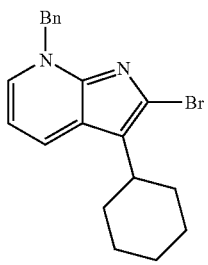

Intermediate 7

7-benzyl-2-bromo-3-cyclohexyl-7H-pyrrolo[2,3-b]pyridine. A 250 mL round bottomed flask was charged with Intermediate 3 (1.85 g, 6.6 mmol) and THF (20 mL). The flask was placed in a water bath at 22° C. and sodium hydride was added in 5 portions (60% dispersion in mineral oil, 400 mg total, 10 mmol). After gas evolution ceased, a $N_2$ inlet was affixed to the flask and the reaction was stirred at r.t. for 30 min before the water bath was replaced with an ice bath. After cooling, benzyl bromide (950 μL, 8 mmol) was added to the reaction dropwise via syringe and the reaction was allowed to warm to r.t. overnight. The reaction was quenched by the addition of $H_2O$ (100 mL), extracted with $CH_2Cl_2$ (250 mL), and the organic phase was washed with brine. Concentration afforded a brown oil which was chromatographed on silica gel (gradient elution: 5%→50% EtOAc in hexanes over 800 mL). Concentration of the second product to elute afforded the title compound as an orange solid (1.9 g, 78% yield). $^1$H NMR (400 MHz, CDCl$_3$) δ ppm 1.26-1.35 (m, 1H) 1.36-1.50 (m, 2H) 1.70-1.92 (m, 7H) 2.85-2.99 (m, 1H) 5.75 (s, 2H) 6.71 (dd, J=7.43, 6.42 Hz, 1H) 7.27-7.34 (m, 5H) 7.38 (d, J=5.29 Hz, 1H) 8.06 (d, J=6.55 Hz, 1H).

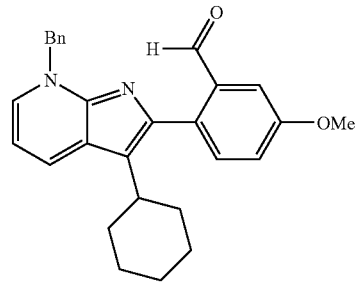

Intermediate 8

2-(7-benzyl-3-cyclohexyl-7H-pyrrolo[2,3-b]pyridin-2-yl)-5-methoxybenzaldehyde. To a suspension of Intermediate 10 (1.95 g, 5.3 mmol) in EtOH (19.5 mL)/toluene (19.5 mL) was added lithium chloride (400 mg, 9.5 mmol), sodium carbonate (1 M aqueous solution, 9 mL, 9 mmol), 2-formyl-4-methoxyphenylboronic acid (1.3 g, 7.2 mmol), and tetrakis (triphenylphosphine)palladium (950 mg, 0.82 mmol). A reflux condenser was affixed and the light orange suspension was refluxed under $N_2$ for 5 h before being cooled to r.t. The reaction was partitioned between 1 N HCl (100 mL) and 1:1 EtOAc/tBME (100 mL) and the organic phase was re-extracted with 1 N HCl (3×15 mL). The combined aqueous phases were basified to pH ~10 with 1 N NaOH and the solution was extracted with $CH_2Cl_2$ (5×50 mL). The $CH_2Cl_2$ layer was concentrated and the residue re-dissolved in $CH_2Cl_2$ (50 mL). A light yellow ppt. formed which was filtered off, and the filtrate was introduced to a silica gel column. Gradient elution with 10%→50% EtOAc in hexanes over 700 mL afforded the title compound as a yellow solid (2.2 g, $^1$H NMR shows the solid is ~20% w/w solvent, therefore 78% yield). LC/MS (ESI) retention time: 1.61 min, m/z 425 (MH+); $^1$H NMR (400 MHz, CDCl$_3$) δ ppm 1.22-1.35 (m, 3H) 1.69-1.88 (m, 7H) 2.65-2.87 (m, 1H) 3.91 (s, 3H) 5.83 (s, 2H) 6.79 (t, J=6.80 Hz, 1H) 7.20 (dd, J=8.56, 2.77 Hz, 1H) 7.32-7.40 (m, 3H) 7.41-7.47 (m, 2H) 7.47-7.60 (m, 3H) 8.20 (d, J=7.05 Hz, 1H) 10.01 (s, 1H).

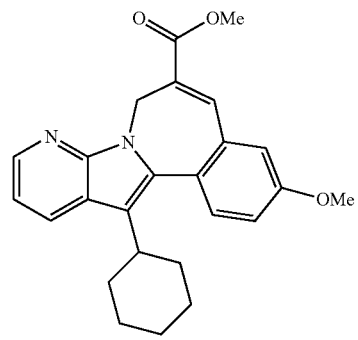

Intermediate 9

Methyl 13-cyclohexyl-3-(methyloxy)-7H-pyrido[3',2':4,5]pyrrolo[2,1-a][2]benzazepine-6-carboxylate. Intermediate 11 (1.4 g, 3.3 mmol) was suspended in methanol (40 mL) and the flask was purged with $N_2$. Palladium hydroxide (wet, 20% Pd, 150 mg) was added, a balloon of $H_2$ was attached, and the suspension was stirred vigorously for 21 h, then filtered through Celite (THF rinse). The filtrate was concentrated to give a brown solid. LC/MS (ESI) retention time: 1.66 min, m/z 335 (MH+).

To a suspension of the crude deprotected product from above in DMF (9 mL) was added Cs$_2$CO$_3$ (900 mg, 2.7 mmol) and methyl 2-(diethoxyphosphoryl)acrylate (900 mg, 4 mmol). The suspension was heated to 60° C. for 3 h, then cooled in an ice bath. Water (50 mL) was added and the resulting yellow ppt. was collected by filtration (H$_2$O rinse) and the excess H$_2$O was removed by EtOH azeotrope to afford 1.4 g of a crude brown oil. Chromatography on silica gel (gradient elution: 10%→50% EtOAc in hexanes over 500 mL) afforded the title compound (1.4 g, 105% yield over 2 steps). $^1$H NMR (400 MHz, CDCl$_3$) δ ppm 1.24-1.42 (m, 3H) 1.65-1.85 (m, 3H) 1.89-2.03 (m, 4H) 2.82 (t, J=11.21 Hz, 1H) 3.80 (s, 3H) 3.83 (s, 3H) 4.1 (br s, 1H) 6.25 (br s, 1H) 6.89-6.99 (m, 2H) 7.03 (dd, J=8.56, 2.77 Hz, 1H) 7.48 (d, J=8.56 Hz, 1H) 7.81 (s, 1H) 8.06 (d, J=6.30 Hz, 1H) 8.29 (d, J=5.04 Hz, 1H).

EXAMPLE 1

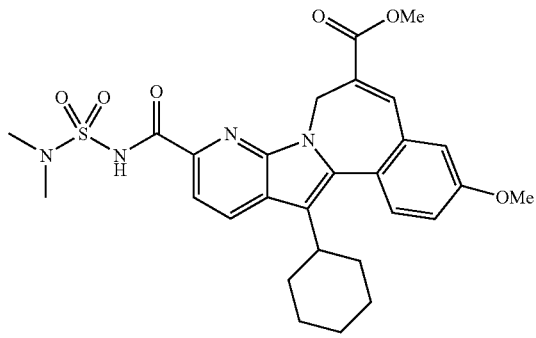

Methyl 13-cyclohexyl-10-((((dimethylamino)sulfonyl)amino)carbonyl)-3-(methyloxy)-7H-pyrido[3',2':4,5]pyrrolo[2,1-a][2]benzazepine-6-carboxylate. To a stirred solution of Intermediate 6 (258 mg, 0.4 mmol) in THF (6 mL) was added H$_2$O (5 mL) and NH$_4$Cl (1.2 g). The biphasic solution was stirred vigorously for 10 min, zinc dust (120 mg, 1.9 mmol) was added, and the suspension stirred for 45 min. The reaction was then filtered through filter paper and partitioned between EtOAc (200 mL) and H$_2$O (20 mL). The organic phase was washed with H$_2$O (2×5 mL) and brine, dried over Na$_2$SO$_4$, filtered, and concentrated to give a crude amber oil. LC/MS (ESI) retention time: 2.27 min, m/z 615 (MH$^+$). The crude product (211 mg, 0.34 mmol) was dissolved in a solution of tetrabutlyammonium fluoride (1 M in THF, 8.5 mL, 8.5 mmol) brought to reflux for 24 h, then cooled to r.t. and partitioned between EtOAc (75 mL) and H$_2$O (10 mL). The organic phase was washed with H$_2$O (3×5 mL) and brine, and dried over Na$_2$SO$_4$. Concentration afforded a crude brown solid which was suspended in DMF (1 mL). Cs$_2$CO$_3$ (200 mg, 0.6 mmol) and methyl 2-(diethoxyphosphoryl)acrylate (200 μL, 0.9 mmol) were added, and the suspension was warmed to 65° C. for 2 h. The reaction was then cooled to r.t., poured into CH$_2$Cl$_2$ (75 mL) and washed with brine. The aqueous phase was re-extracted with CH$_2$Cl$_2$ (2×15 mL), and the combined organic phases were dried (Na$_2$SO$_4$), filtered, and concentrated to give a brown oil. Chromatography on silica gel (gradient elution: 10% EtOAc in C$_6$H$_{14}$ for 100 mL, then→35% over 800 mL) afforded the product as a yellow solid (72 mg, 38% yield from Intermediate 6). LC/MS (ESI) retention time: 2.23 min, m/z 553 (MH$^+$); $^1$H NMR (400 MHz, CDCl$_3$) δ ppm 1.27-1.48 (m, 3H) 1.48-1.63 (m, 1H) 1.68-1.82 (m, 2H) 1.84-2.01 (m, 4H) 2.76-2.93 (m, 1H) 3.07 (s, 6H) 3.88 (s, 3H) 3.92 (s, 3H) 4.10 (br s, 1H) 6.22 (br s, 1H) 7.02 (d, J=2.52 Hz, 1H) 7.11 (dd, J=8.56, 2.77 Hz, 1H) 7.54 (d, J=8.56 Hz, 1H) 7.86 (s, 1 H) 7.92 (d, J=8.31 Hz, 1H) 8.24 (d, J=8.31 Hz, 1H).

EXAMPLE 2

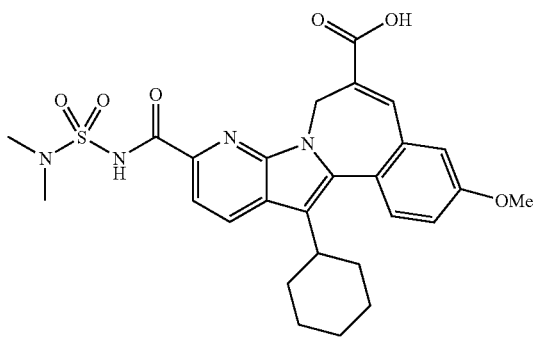

13-Cyclohexyl-10-((((dimethylamino)sulfonyl)amino)carbonyl)-3-(methyloxy)-7H-pyrido[3',2':4,5]pyrrolo[2,1-a][2]benzazepine-6-carboxylic acid. A sodium hydroxide solution (1 N, 350 μL) was added to a stirred solution of Intermediate 7 (96 mg) in THF (1 mL) and the reaction was refluxed for 10 min, cooled to r.t., and quenched with HCl (1 N, 700 μL). The reaction was extracted with EtOAc (50 mL), and the organic phase was washed with H$_2$O (2×5 mL) and brine. The combined aqueous phases were re-extracted with EtOAc (25 mL), and the organic phase washed with brine. The combined organic phases were dried over Na$_2$SO$_4$, filtered, and concentrated to give 95 mg of a yellow solid. LC/MS (ESI) retention time: 2.13 min, m/z 539 (MH$^+$).

EXAMPLE 3

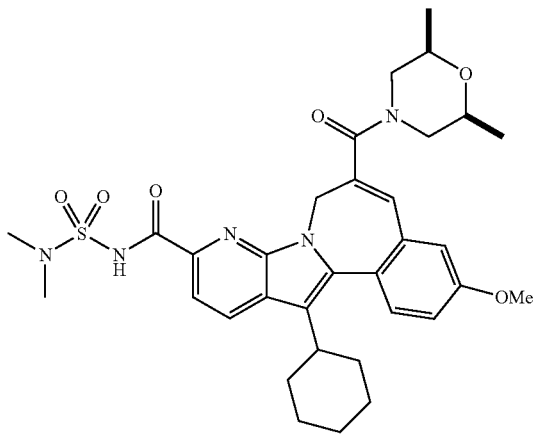

13-Cyclohexyl-N-((dimethylamino)sulfonyl)-6-(((2R,6S)-2,6-dimethyl-4-morpholinyl)carbonyl)-3-(methyloxy)-7H-pyrido[3',2':4,5]pyrrolo[2,1-a][2]benzazepine-10-carboxamide. To a stirred suspension of Intermediate 8 (28 mg, 44 µmol) in CH$_2$Cl$_2$ (500 µL) was added HATU (24 mg, 63 µmol) and (2R,6S)-2,6-dimethylmorpholine (20 µL, 150 µmol). The homogeneous solution was allowed to stir at r.t. for 1 h, then filtered through sand (CH$_2$Cl$_2$ rinse) and introduced to a silica gel column. Gradient elution with 10%→100% EtOAc in C$_6$H$_{14}$ over 570 mL afforded the title compound as a pale yellow solid (19 mg, 68% yield). LC/MS (ESI) retention time: 2.08 min, m/z 636 (MH$^+$); $^1$H NMR (400 MHz, CDCl$_3$) δ ppm 1.50-1.66 (m, 3H) 1.72-1.85 (m, 2H) 1.85-2.13 (m, 4H) 2.37-2.57 (m, 2H) 2.80-2.94 (m, 1H) 3.06 (s, 6H) 3.47 (br s, 1H) 3.91 (s, 3H) 4.35 (br s, 2H) 5.55 (br s, 1 H) 6.83 (br s, 1H) 6.93 (d, J=2.52 Hz, 1H) 7.06 (dd, J=8.69, 2.64 Hz, 1H) 7.50 (d, J=8.56 Hz, 1H) 7.97 (d, J=8.3 1 Hz, 1H) 8.27 (d, J=8.06 Hz, 1H) 10.03 (s, 1H).

EXAMPLE 4

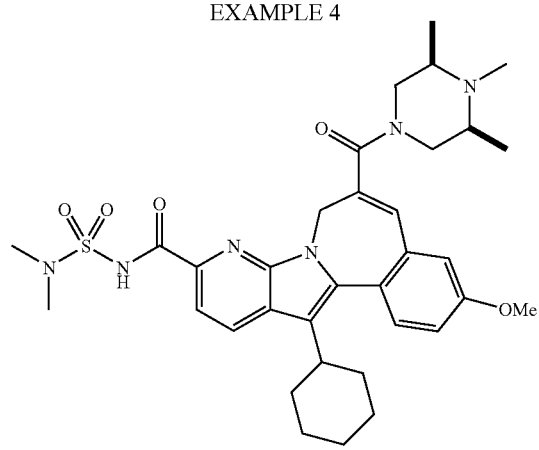

13-cyclohexyl-N-((dimethylamino)sulfonyl)-3-(methyloxy)-6-(((3R,5S)-3,4,5-trimethyl-1-piperazinyl)carbonyl)-7H-pyrido[3',2':4,5]pyrrolo[2,1-a][2]benzazepine-10-carboxamide. A solution of Intermediate 8 (10 mg, 18 µmol), (2R,6S)-1,2,6-trimethylpiperazine bis(trifluoroacetate) (7.5 mg, 21 µmol), HATU (11 mg, 29 µmol), and N,N-diisopropylethylamine (20 µL, 110 µmol) in CH$_2$Cl$_2$ was stirred at r.t. for 2 h, then loaded directly onto a preparative TLC plate. After allowing the volatiles to evaporate, the plate was eluted with 4% MeOH in CH$_2$Cl$_2$ and the major UV$^+$ band was scraped from the plate. The product was eluted from the silica gel with 14% MeOH in CH$_2$Cl$_2$. Concentration afforded the title compound as a yellow solid (9 mg, 76% yield). LC/MS (ESI) retention time: 1.75 min, m/z 649 (MH$^+$); $^1$H NMR (400 MHz, CD$_3$OD) δ ppm 1.02-1.12 (m, 1H) 1.21-1.39 (m, 10 H) 1.40-1.54 (m, 3H) 1.71-1.83 (m, 2H) 1.89-2.14 (m, 4H) 2.13-2.24 (m, 2H) 2.23-2.36 (m, 1H) 2.51-2.73 (m, 2H) 2.86-2.97 (m, 1H) 3.01 (s, 6H) 3.91 (s, 3 H) 4.34 (br d, 1H) 5.78 (br d, 1H) 6.91 (s, 1H) 7.08 (d, J=2.27 Hz, 1H) 7.15 (dd, J=8.56, 2.52 Hz, 1H) 7.58 (d, J=8.56 Hz, 1H) 7.93 (d, J=8.31 Hz, 1H) 8.38 (d, J=8.31 Hz, 1H).

EXAMPLE 5

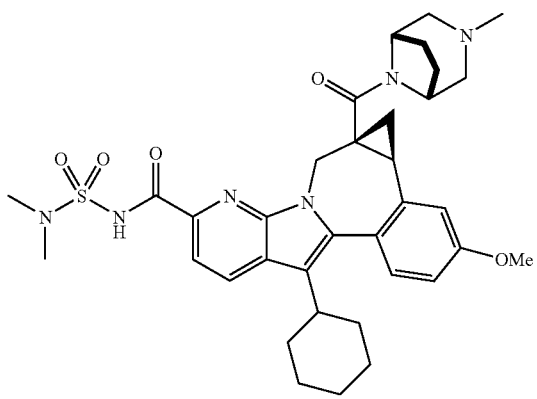

(+/−)-(1aR,12bS)-8-Cyclohexyl-N-((dimethylamino)sulfonyl)-1a-((3-methyl-3,8-diazabicyclo[3.2.1]oct-8-yl)carbonyl)-11-(methyloxy)-1,1a,2,12b-tetrahydrocyclopropa[d]pyrido[3',2':4,5]pyrrolo[2,1-a][2]benzazepine-5-carboxamide. Sodium hydride (60% suspension in mineral oil, 10 mg, 250 µumol) was added to a stirred suspension of Intermediate 7 (17 mg, 31 µmol) and trimethylsulfoxonium iodide (30 mg, 140 µmol) in DMSO (750 µL). After 45 min, all the yellow solid had dissolved. Water (100 µL) was added and the reaction was allowed to stir for 30 min before being partitioned between EtOAc and 0.1 N HCl. The organic phase was washed with brine, dried over Na$_2$SO$_4$, filtered, and concentrated to give the crude cyclopropyl carboxylic acid as a yellow powder. LC/MS (ESI) retention time: 2.14 min, m/z 553 (MH$^+$). To this crude carboxylic acid was added CH$_3$CN (500 µL), N,N-diisopropylethylamine (50 µL), TBTU (25 mg, 78 µmol), and 3-methyl-3,8-diazabicyclo[3.2.1]octane dihydrochloride (15 mg, 75 µmol). The reaction was allowed to stir at r.t. for 3 h, then partitioned between CH$_2$Cl$_2$ (50 mL) and sat'd NaHCO$_3$ (5 mL). The aqueous phase was re-extracted with CH$_2$Cl$_2$ (2×5 mL) and the combined organic phases were dried over Na$_2$SO$_4$. Filtration and concentration afforded a yellow residue which was purified by prep TLC, elution with 2% MeOH/2% AcOH in CH$_2$Cl$_2$. The middle of the major UV$^+$ band was scraped from the plate and the product was eluted from the silica gel with 10% MeOH in CH$_2$Cl$_2$. Concentration of the volatiles afforded the title compound (9 mg, 44% yield). LC/MS (ESI) retention time: 1.83 min, m/z 661 (MH$^+$); $^1$H NMR as a 1:1 mixture of atropisomers (400 MHz, CDCl$_3$) δ ppm 0.49-0.52 (m, 0.5H) 0.81-0.88 (m, 1.5H) 1.18-1.33 (m, 6H) 1.34-1.50 (m, 3H) 1.59 (m, 1.5H) 1.77 (m, 3 H) 1.84-2.04 (m, 7H) 2.18-2.38 (m, 3H) 2.44 (m, 1H) 2.47-2.55 (m, 1H) 2.56-2.62 (m, 0.5H) 2.62-2.74 (m, 1H) 2.76-2.90 (m, 1H) 2.92-3.00 (m, 1H) 3.04 (s, 3H) 3.07 (s, 3H) 3.42 (d, J=14.60 Hz, 0.5H) 3.90 (s, 3H) 4.08 (d, J=14.35 Hz, 0.5 H) 4.26 (br s, 0.5H) 4.41 (br s, 0.5H) 4.61 (br s, 0.5H) 5.36 (br s, 0.5H) 5.49-5.84 (br d, 0.5H) 6.90 (dd, J=8.56, 2.52 Hz, 0.5H) 6.95 (dd, J=8.44, 2.14 Hz, 0.5H) 7.09 (d, J=2.27 Hz, 0.5H) 7.14 (s, 0.5H) 7.25-7.32 (m, 1H) 7.93 (d, J=8.06 Hz, 0.5H) 7.99 (d, J=8.06 Hz, 0.5H) 8.16-8.29 (m, 1H).

EXAMPLE 6

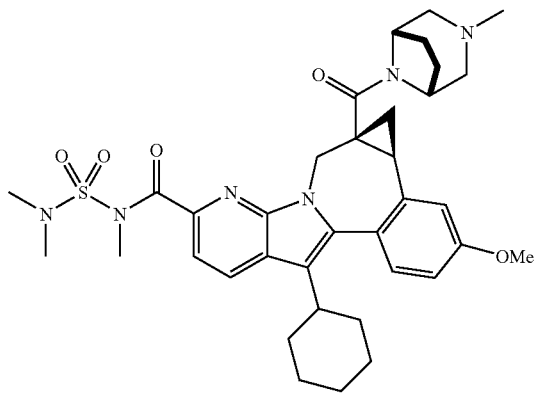

(+/−)-(1aR,12bS)-8-Cyclohexyl-N-((dimethylamino)sulfonyl)-N-methyl-1a-((3-methyl-3,8-diazabicyclo[3.2.1]oct-8-yl)carbonyl)-11-(methyloxy)-1,1a,2,12b-tetrahydrocyclopropa[d]pyrido[3',2':4,5]pyrrolo[2,1-a][2]benzazepine-5-carboxamide. To a solution of (±)-(1aR,12bS)-8-Cyclohexyl-N-((dimethylamino)sulfonyl)-1a-((3-methyl-3,8-diazabicyclo[3.2.1]oct-8-yl)carbonyl)-11-(methyloxy)-1,1a,2,12b-tetrahydrocyclopropa[d]pyrido[3',2':4,5]pyrrolo[2,1-a][2]benzazepine-5-carboxamide (21.9 mg, 33 µmol) in THF (250 µL)/MeOH (50 µL) was added triphenylphosphine (50 mg, 0.19 mmol) and DEAD (30 µL, 0.19 mmol). The reaction was allowed to stir at r.t. for 2.5 h, then the volatiles were evaporated and the residue purified by silica gel chromatography. Gradient elution with 1%→4% MeOH in CH$_2$Cl$_2$ over 240 mL delivered a single broad peak. Collection of the middle fraction (12 mL) of the peak and concentration afforded the title compound as a yellow film (3.4 mg, 15% yield). LC/MS (ESI) retention time: 1.81 min, m/z 675 (MH$^+$); $^1$H NMR as a 3:2 mixture of atropisomers (400 MHz, CDCl$_3$) δ ppm 0.43 (t, J=6.04 Hz, 0.6H) 0.76-0.95 (m, 2H) 1.14-1.49 (m, 6.4H) 1.77 (m, 2.6H) 1.83-2.12 (m, 7.4H) 2.13-2.45 (m, 3H) 2.51-2.77 (m, 2H) 2.78-2.90 (m, 1H) 2.98-3.07 (m, 6H) 3.39 (d, J=14.60 Hz, 0.4H) 3.46-3.50 (m, 3H) 3.89 (s, 3H) 4.03 (m, 0.6H) 4.36 (m, 0.4H) 4.58 (br s, 0.6H) 5.49 (br s, 0.4H) 5.70-5.73 (m, 0.4H) 6.89 (dd, J=8.56, 2.77 Hz, 0.6H) 6.95 (dd, J=8.44, 2.64 Hz, 0.4 H) 7.07-7.18 (m, 1H) 7.26-7.33 (m, 1H) 7.47 (d, J=8.06 Hz, 0.6H) 7.51-7.60 (m, 0.4H) 8.14-8.19 (m, 1H).

EXAMPLE 7

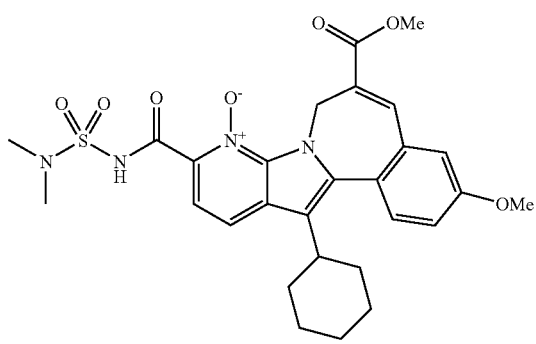

Methyl 13-cyclohexyl-10-((((dimethylamino)sulfonyl)amino)carbonyl)-3-(methyloxy)-7H-pyrido[3',2':4,5]pyrrolo[2,1-a][2]benzazepine-6-carboxylate 9-oxide. To a stirred solution of Intermediate 6 (250 mg, 0.4 mmol) in THF (10 mL) was a TBAF solution (1.0 M in THF, 10 mL, 10 mmol) and the resulting solution was heated to reflux for 22 hrs. Upon cooling, the reaction was diluted with EtOAc (250 mL), washed with H$_2$O (7×15 mL) and brine, dried over Na$_2$SO$_4$, filtered, and concentrated to give the intermediate deprotected indole as a brown foam (252 mg, LC/MS (ESI) retention time: 2.01 min, m/z 501 (MH$^+$)) which was used in the next step without further purification.

To a solution of the crude aldehyde from above (252 mg) in DMF (1.5 mL) was added Cs$_2$CO$_3$ (325 mg, 1 mmol) and methyl 2-(diethoxyphosphoryl)acrylate (250 µL, 1.1 mmol). The reaction was heated to 65° C. for 2 h, then diluted with H$_2$O (10 mL). The homogenous solution was neutralized with 0.1 N HCl, and the resulting brown ppt. was collected by filtration, rinsed with H$_2$O, and dried by co-evaporation with EtOH to give a yellow oil. Purification by silica gel chromatography (gradient elution: 10%→50% EtOAc in hexanes over 900 mL) afforded the title compound as a brown oil (93 mg, 41% yield over 2 steps). LC/MS (ESI) retention time: 2.13 min, m/z 569 (MH$^+$); $^1$H NMR (400 MHz, CDCl$_3$) δ ppm 1.27-1.42 (m, 2H) 1.46-1.62 (m, 1H) 1.69-1.98 (m, 7H) 2.67-2.81 (m, 1H) 3.04 (s, 6H) 3.87 (s, 3H) 3.91 (s, 3H) 7.01 (d, J=2.52 Hz, 1H) 7.10 (dd, J=8.69, 2.64 Hz, 1H) 7.45 (d, J=8.56 Hz, 1H) 7.62 (s, 1H) 7.83-7.93 (m, 2H) 8.02 (d, J=8.56 Hz, 1H) 14.93 (s, 1H).

EXAMPLE 8

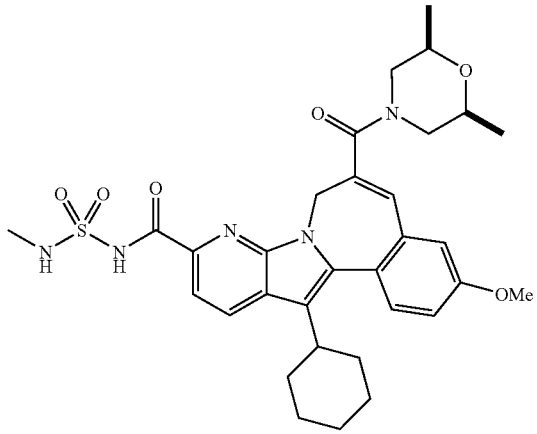

13-Cyclohexyl-N-((methylamino)sulfonyl)-6-(((2R,6S)-2,6-dimethyl-4-morpholinyl)carbonyl)-3-(methyloxy)-7H-pyrido[3',2':4,5]pyrrolo[2,1-a][2]benzazepine-10-carboxamide. To a stirred solution of Intermediate 9 (44 mg, 77 µmol) in THF (1.0 mL) was added an aqueous sodium hydroxide solution (1 N, 100 µL, 100 µmol) and the reaction was refluxed for 1 h. An additional portion of the sodium hydroxide solution (50 µL, 50 µmol) was added and reflux was resumed for 15 min, at which point the reaction was cooled to r.t. and poured into a biphasic mixture of EtOAc (50 mL), 1 N HCl (175 µL), and H$_2$O (5 mL). The organic phase was washed with H$_2$O (5 mL) and brine, dried over Na$_2$SO$_4$, filtered, and concentrated to give the crude carboxylic acid as a yellow glass (41 mg). LC/MS (ESI) retention time: 2.03 min, m/z 555 (MH$^+$)

To a stirred suspension of the crude carboxylic acid from above (41 mg, 74 µmol) in CH$_2$Cl$_2$ (1.0 mL) was added iPr$_2$NEt (100 µL, 0.57 mmol), TBTU (30 mg, 93 µmol) and (2R,6S)-2,6-dimethylmorpholine (20 µL, 150 µmol). The reaction was allowed stir at r.t. for 2 h, and then was partitioned between CH$_2$Cl$_2$ and H$_2$O. The organic phases was re-extracted with CH$_2$Cl$_2$ and the combined organic phases were washed with brine, dried over Na$_2$SO$_4$, filtered, and concentrated to give a yellow glass. Silica gel chromatography (gradient elution, 0%→100% B:A over 600 mL; eluent A: CH$_2$Cl$_2$, eluent B: 2% MeOH in EtOAc) afforded a mixture, which was purified by prep TLC (elute w/ 2% HOAc/ 20% EtOAc in hexanes). Collection of the minor UV+ band afforded 5 mg of the title compound. LC/MS (ESI) retention time: 3.22 min, m/z 622 (MH$^+$); $^1$H NMR (400 MHz, CDCl$_3$) δ ppm 1.63-1.73 (m, 2H) 1.74-1.82 (m, 2H) 1.85-2.03 (m, 4H) 2.48 (br s, 1H) 2.74-2.82 (m, 5H) 2.87-2.95 (m, 1H) 3.48 (br s, 1H) 3.91 (s, 3H) 4.34 (br s, 1H) 5.30 (q, J=5.29 Hz, 1 H, exchanges w/ D$_2$O) 5.57 (br s, 1H) 6.74-6.87 (m, 1H) 6.93 (d, J=2.77 Hz, 1H) 7.07 (dd, J=8.56, 2.77 Hz, 1H) 7.50 (d, J=8.81 Hz, 1H) 7.97 (d, J=8.06 Hz, 1 H) 8.28 (d, J=8.06 Hz, 1H) 10.10 (s, 1H).

EXAMPLE 9

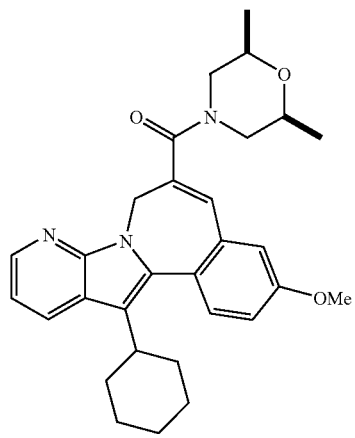

13-Cyclohexyl-6-(((2R,6S)-2,6-dimethyl-4-morpholinyl) carbonyl)-3-(methyloxy)-7H-pyrido[3',2':4,5]pyrrolo[2,1-a] [2]benzazepine. To a stirred solution of Intermediate 12 (100 mg, 0.25 mmol) in THF (15 mL) was added H$_2$O (3 mL) and 1 N NaOH (1 mL, 1 mmol). The reaction was stirred overnight at r.t., then quenched with 1 mL of 1 N HCl. The reaction was partitioned between EtOAc and sat'd NaHCO$_3$, and the aqueous phase was re-extracted twice with EtOAc. The combined organic phases were dried (brine, Na$_2$SO$_4$), filtered, and concentrated to give a yellow glass.

To a 15 mL round bottomed flask containing the crude carboxylic acid from above (118 mg, 0.3 mmol) in CH$_2$Cl$_2$ (2.0 mL) were added iPr$_2$NEt (250 µL, 1.4 mmol), (2R,6S)-2,6-dimethylmorpholine (50 µL, 0.4 mmol), HOBt (53 mg, 0.4 mmol), and EDC HCl (75 mg, 0.4 mmol). The reaction was stirred at r.t. for 20 h, diluted with CH$_2$Cl$_2$, filtered, and the filtrate was chromatographed on silica gel (gradient elution: 10%→100% EtOAc in hexanes over 700 mL). The fractions were combined and re-chromatographed on silica gel (gradient elution: 0%→10% MeOH in CH$_2$Cl$_2$ over 500 mL) to afford, after fraction collection and concentration, the title compound as a yellow foam (77 mg, 63% yield over two steps). LC/MS (ESI) retention time: 2.06 min, m/z 486 (MH$^+$); $^1$H NMR (400 MHz, CDCl$_3$) δ ppm 0.35 (br s, 2H) 1.06-1.25 (m, 3H) 1.26-1.47 (m, 3H) 1.58 (br s, 1H) 1.74-1.78 (m, 2 H) 1.83-2.15 (m, 4H) 2.40 (br s, 2H) 2.72 (br s, 1H) 2.80-2.98 (m, 1H) 3.52 (br s, 1H) 3.88 (s, 3H) 4.35 (br s, 2H) 5.60 (br s, 1H) 6.78 (s, 1H) 6.90 (s, 1H) 6.95-7.08 (m, 2H) 7.47 (d, J=8.56 Hz, 1H) 8.12 (d, J=7.81 Hz, 1H) 8.25 (d, J=3.78 Hz, 1 H).

What is claimed is:

1. A compound of formula I

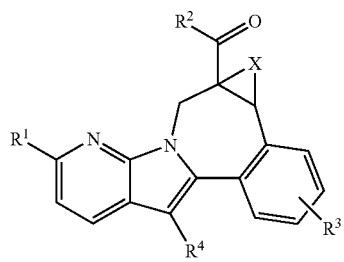

where:

R$^1$ is H, CO$_2$R$^5$ or CONR$^6$R$^7$;

R$^2$ is hydroxy, alkoxy, amino, alkylamino, dialkylamino;

or R$^2$ is azetidinyl, pyrrolidinyl, piperidinyl, piperazinyl, morpholinyl, homopiperidinyl, or homomorpholinyl, and is substituted with 0-3 substituents selected from alkyl and alkoxy;

or R$^2$ is

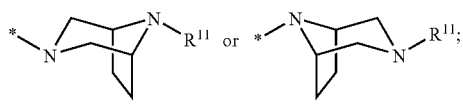

R$^3$ is hydrogen, halo, alkyl, alkenyl, hydroxy, benzyloxy, or alkoxy;

R$^4$ is cycloalkyl;

R$^5$ is hydrogen or alkyl;

R$^6$ is hydrogen, alkyl, alkylSO$_2$, cycloalkylSO$_2$, haloalkylSO$_2$, (R$^8$)$_2$NSO$_2$, or (R$^9$)SO$_2$;

R$^7$ is hydrogen or alkyl;

R$^8$ is hydrogen or alkyl;

R$^9$ is azetidinyl, pyrrolidinyl, piperidinyl, N-(R$^{10}$)piperazinyl, morpholinyl, thiomorpholinyl, homopiperidinyl, or homomorpholinyl;

R$^{10}$ is hydrogen or alkyl;

R$^{11}$ is hydrogen, alkyl, cycloalkyl, (cycloalkyl)alkyl, benzyl, alkylcarbonyl, alkoxycarbonyl, benzyloxycarbonyl, (R$^8$)$_2$NCO, alkylSO$_2$, or pyridinyl; and X is absent (forming a compound of formula Ia), a bond (forming a compound of formula Ib), or methylene (forming a compound of formula Ic);

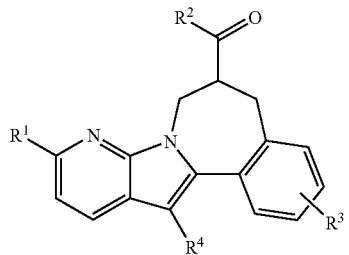

(Ia)

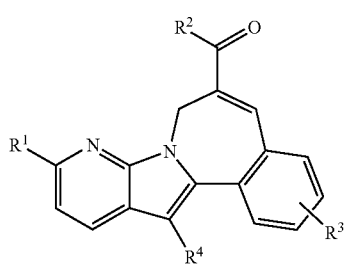

(Ib)

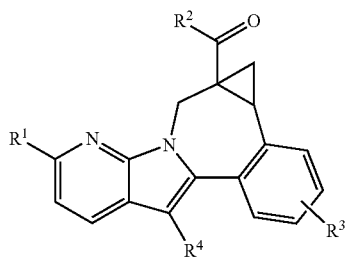

(Ic)

or a pharmaceutically acceptable salt thereof.

2. A compound of claim 1, where $R^1$ is $CONR^6R^7$; $R^6$ is alkylSO$_2$, cycloalkylSO$_2$, haloalkylSO$_2$, $(R^8)_2$NSO$_2$, or $(R^9)$SO$_2$; and $R^7$ is hydrogen.

3. A compound of claim 1, where $R^2$ is dimethylamino, pyrrolidinyl, morpholinyl, dimethylmorpholinyl, piperazinyl, trimethylpiperazinyl, or

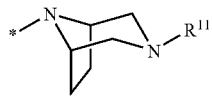

where $R^{11}$ is methyl.

4. A compound of claim 1, where $R^3$ is hydrogen.
5. A compound of claim 1, where $R^3$ methoxy.
6. A compound of claim 1, where $R^4$ is cyclohexyl.
7. A compound of claim 1, where $R^6$ is $(R^8)_2$NSO$_2$ or $(R^9)$SO$_2$.
8. A compound of claim 1, where X is absent.
9. A compound of claim 1, where X is a bond.
10. A compound of claim 1, where X is methylene.

11. A compound of claim 1, selected from the group consisting of

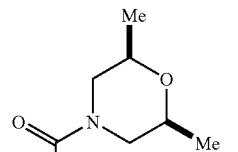

or a pharmaceutically acceptable salt thereof.

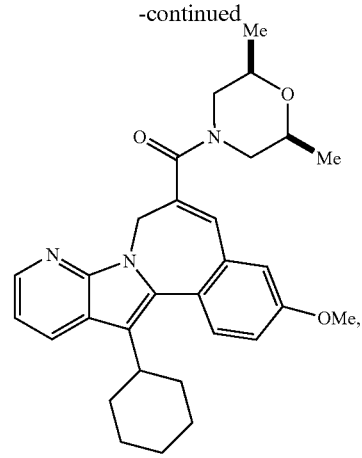

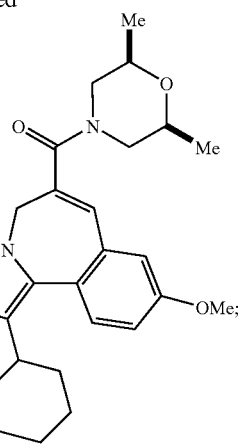

or a pharmaceutically acceptable salt thereof.

12. A composition comprising a compound of claim 1, or a pharmaceutically acceptable salt thereof, and a pharmaceutically acceptable carrier.

13. A method of treating hepatitis C infection comprising administering a therapeutically effective amount of a compound of claim 1, or a pharmaceutically acceptable salt thereof, to a patient.

* * * * *

UNITED STATES PATENT AND TRADEMARK OFFICE
CERTIFICATE OF CORRECTION

PATENT NO. : 7,517,872 B2  
APPLICATION NO. : 12/031844  
DATED : April 14, 2009  
INVENTOR(S) : Andrew Nickel et al.

Page 1 of 1

It is certified that error appears in the above-identified patent and that said Letters Patent is hereby corrected as shown below:

In the Claims:

Claim 5:

Column 37, line 60, after "$R^3$", insert -- is --.

Signed and Sealed this
Twelfth Day of April, 2011

David J. Kappos
*Director of the United States Patent and Trademark Office*